(12) United States Patent
Nakaoka et al.

(10) Patent No.: US 8,808,265 B2
(45) Date of Patent: Aug. 19, 2014

(54) PANTS-TYPE DISPOSABLE DIAPER

(75) Inventors: Kenji Nakaoka, Osaka (JP); Yuki Takahashi, Tsurugi-cho (JP)

(73) Assignee: Livedo Corporation, Shikokuchuo (JP)

( * ) Notice: Subject to any disclaimer, the term of this patent is extended or adjusted under 35 U.S.C. 154(b) by 209 days.

(21) Appl. No.: 13/376,535

(22) PCT Filed: Jul. 13, 2010

(86) PCT No.: PCT/JP2010/004536
§ 371 (c)(1),
(2), (4) Date: Dec. 6, 2011

(87) PCT Pub. No.: WO2011/018877
PCT Pub. Date: Feb. 17, 2011

(65) Prior Publication Data
US 2012/0078213 A1   Mar. 29, 2012

(30) Foreign Application Priority Data

Aug. 13, 2009   (JP) .................. 2009-187779

(51) Int. Cl.
*A61F 13/496* (2006.01)
*A61F 13/49* (2006.01)
*A61F 13/495* (2006.01)

(52) U.S. Cl.
CPC ......... *A61F 13/496* (2013.01); *A61F 13/49019* (2013.01); *A61F 13/49017* (2013.01); *A61F 13/495* (2013.01)
USPC .................................................... 604/385.25

(58) Field of Classification Search
USPC ........................................ 604/385.24, 385.25
See application file for complete search history.

(56) References Cited

U.S. PATENT DOCUMENTS

| 5,836,931 A | 11/1998 | Toyoda et al. |
| 7,226,438 B2 * | 6/2007 | Soga et al. ............... 604/385.25 |

(Continued)

FOREIGN PATENT DOCUMENTS

| DE | 102007002290 A1 | 7/2008 |
| EP | 1997464 A1 | 12/2008 |

(Continued)

OTHER PUBLICATIONS

Japanese Office Action dated Jun. 4, 2013, issued in corresponding Japanese Patent Application No. 2009-187779, with English translation (5 pages).

(Continued)

*Primary Examiner* — Susan Su
(74) *Attorney, Agent, or Firm* — Westerman, Hattori, Daniels & Adrian, LLP

(57) ABSTRACT

A pants-type disposable diaper 1 comprising: a diaper main body 2 having a front part P, a back part Q, and a crotch part R therebetween, and having a waist opening 3 and a pair of leg openings 4; an absorbent core 10 disposed at the crotch part R; a first elastic member 13 having a first crotch-crossing part 13A which extends intermittently across the crotch part R and a first leg opening edge part 13B which extends along edges 15 of a front side of the both leg openings 4; and a second elastic member 14 disposed continuously so as to be spaced from the first elastic member 13, and having a second crotch-crossing part 14A which extends across the crotch part R and a second leg opening edge part 14B which extends along edges 15 of a back side of the both leg openings 4.

6 Claims, 4 Drawing Sheets

(56) References Cited

U.S. PATENT DOCUMENTS

| | | | |
|---|---|---|---|
| 7,530,972 B2* | 5/2009 | Ando et al. | 604/385.27 |
| 7,777,094 B2* | 8/2010 | Mori et al. | 604/367 |
| 2002/0007172 A1* | 1/2002 | Takei et al. | 604/385.27 |
| 2002/0049421 A1* | 4/2002 | Hayase et al. | 604/385.27 |
| 2002/0068919 A1* | 6/2002 | Shinohara et al. | 604/385.27 |
| 2002/0072728 A1* | 6/2002 | Shinohara et al. | 604/385.29 |
| 2003/0000620 A1* | 1/2003 | Herrin et al. | 156/62.2 |
| 2003/0078556 A1* | 4/2003 | Sasaki et al. | 604/385.25 |
| 2003/0083638 A1* | 5/2003 | Molee | 604/385.27 |
| 2003/0196253 A1* | 10/2003 | Rajala et al. | 2/401 |
| 2004/0035521 A1* | 2/2004 | Nakakado et al. | 156/229 |
| 2004/0133180 A1* | 7/2004 | Mori et al. | 604/385.25 |
| 2005/0004548 A1* | 1/2005 | Otsubo et al. | 604/385.25 |
| 2006/0064069 A1* | 3/2006 | Rajala et al. | 604/385.24 |
| 2006/0174400 A1* | 8/2006 | Kurata | 2/400 |
| 2008/0027406 A1* | 1/2008 | Shirai et al. | 604/385.24 |
| 2008/0065036 A1* | 3/2008 | Minato et al. | 604/367 |
| 2008/0071241 A1 | 3/2008 | Bittner et al. | |
| 2008/0300565 A1* | 12/2008 | Takahashi et al. | 604/367 |
| 2008/0300568 A1 | 12/2008 | Fujioka et al. | |
| 2009/0005751 A1* | 1/2009 | Shirai et al. | 604/385.29 |
| 2009/0088718 A1* | 4/2009 | Toyoshima et al. | 604/385.23 |
| 2009/0177176 A1* | 7/2009 | Saito | 604/385.29 |
| 2009/0204094 A1 | 8/2009 | Bittner et al. | |
| 2009/0275911 A1 | 11/2009 | Hornung et al. | |
| 2009/0299319 A1* | 12/2009 | Takahashi et al. | 604/385.25 |
| 2010/0022983 A1 | 1/2010 | Bittner et al. | |
| 2010/0076394 A1* | 3/2010 | Hayase et al. | 604/385.29 |
| 2010/0094239 A1* | 4/2010 | Nakaoka et al. | 604/385.25 |
| 2010/0286646 A1* | 11/2010 | Takino et al. | 604/385.3 |
| 2010/0318053 A1* | 12/2010 | Smet | 604/385.23 |

FOREIGN PATENT DOCUMENTS

| | | |
|---|---|---|
| JP | 6-296643 A | 10/1994 |
| JP | 2002-172132 A | 6/2002 |
| JP | 2006-149749 A | 6/2006 |
| JP | 2008-253288 A | 10/2008 |

OTHER PUBLICATIONS

International Search Report of PCT/JP2010/004536, mailing date Oct. 26, 2010.

Japanese Office Action dated Feb. 4, 2014, issued in Japanese Patent Application No. 2009-187779, w/English translation, (6 pages).

* cited by examiner

PANTS-TYPE DISPOSABLE DIAPER

TECHNICAL FIELD

The present invention relates to a pants-type disposable diaper for an infant or an adult.

BACKGROUND ART

Conventionally, there is known a pants-type disposable diaper. For example, Japanese Laid-Open Patent Publication No. 6-296643 (Patent Literature 1) discloses a pants-type disposable diaper comprising a first elastic member disposed continuously so as to extend across a crotch part and along edges of a front side of both leg openings, and a second elastic member disposed continuously so as to extend across the crotch part and along edges of a back side of the both leg openings.

CITATION LIST

Patent Literature

Patent Literature 1
Japanese Laid-Open Patent Publication No. 6-296643

SUMMARY OF INVENTION

Technical Problem

In a conventional pants-type disposable diaper, when a wearer excretes loose stool or diarrhea stool containing a large amount of water, the loose stool or the diarrhea stool may spread in a wide range on the diaper so as to make the buttocks of the wearer dirty in a wide range, and may laterally leak from the diaper. The present invention has been achieved in view of the above circumstances, and an object of the present invention is to provide a pants-type disposable diaper which is able to receive loose stool or diarrhea stool appropriately.

Solution to Problem

The pants-type disposable diaper of the present invention which solves the above problems comprises: a diaper main body having a front part, a back part, and a crotch part positioned between the front part and the back part, and having a waist opening and a pair of leg openings formed by joining the front part and the back part; an absorbent core disposed at the crotch part; a first elastic member disposed to the diaper main body, and having a first crotch-crossing part which extends intermittently across the crotch part and a first leg opening edge part which extends along edges of a front side of the both leg openings; and a second elastic member disposed continuously to the diaper main body so as to be spaced from the first elastic member, and having a second crotch-crossing part which extends across the crotch part and a second leg opening edge part which extends along edges of a back side of the both leg openings.

In the pants-type disposable diaper of the present invention, a pocket is formed at a bottom of the diaper or on a back side of the diaper by the second elastic member, and the pocket can receive loose stool or diarrhea stool. Therefore, loose stool or diarrhea stool are less likely to spread in a wide range on the diaper, thereby alleviating discomfort to a wearer or a caregiver. In addition, lateral leakage of loose stool or diarrhea stool from the diaper is less likely to occur.

A frontmost part of the second crotch-crossing part is preferably located at a region of 90 mm or less anterior and 40 mm or less posterior to a center of the diaper main body in a front-back direction. According to this structure, loose stool or diarrhea stool are tend to be received appropriately in the pocket formed by the second elastic member.

The second elastic member is preferably spaced from the first elastic member at a distance of 10 mm or more and 50 mm or less. According to this structure, leg gathers are formed along the edges of the both leg openings appropriately, thereby preventing leakage of excrement such as urine, loose stool and the like from the crotch part. Further, stretching and contracting of the second elastic member are less likely to be impaired by the first elastic member, and therefore, the pocket is easy to be formed by the second elastic member appropriately.

Advantageous Effects of Invention

The pants-type disposable diaper of the present invention can receive loose stool or diarrhea stool appropriately.

DESCRIPTION OF EMBODIMENTS

Figure 1:
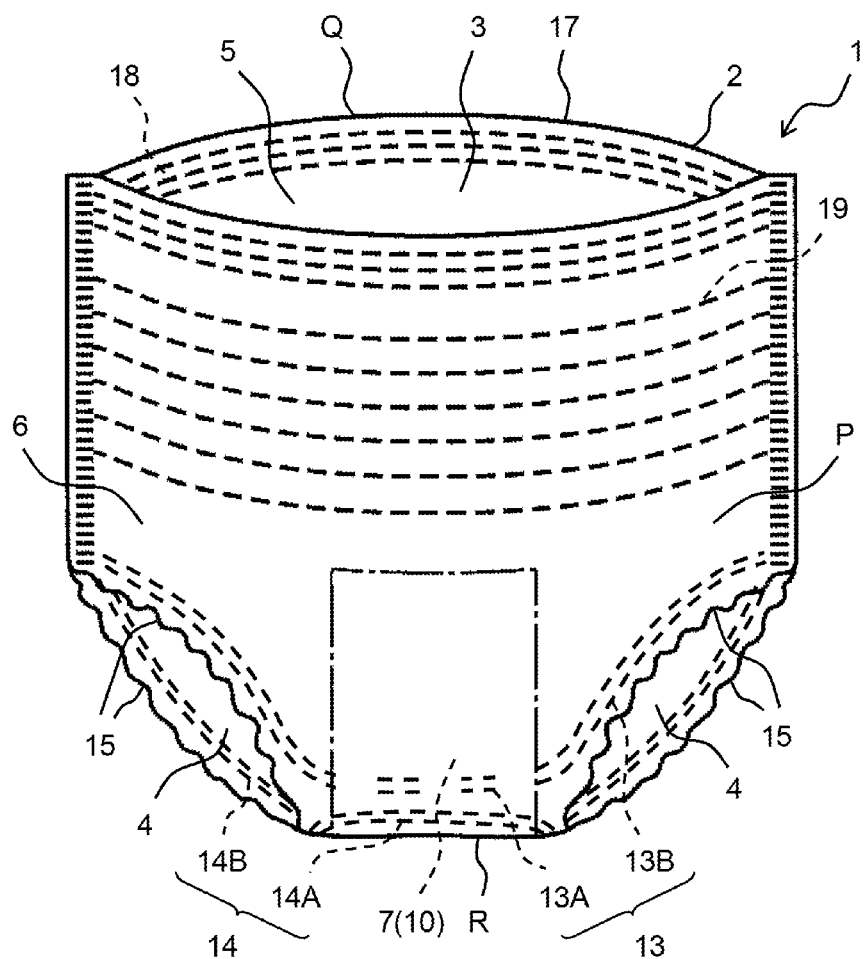
FIG. 1 shows a perspective view of a pants-type disposable diaper of the present invention.

A pants-type disposable diaper of the present invention comprises a diaper main body having a front part, a back part, and a crotch part positioned between the front part and the back part. In the diaper main body, a waist opening and a pair of leg openings are formed by joining the front part and the back part. In detail, the front part and the back part are joined at their both side edges in a width direction of the diaper, thereby forming the pair of leg openings on both sides of the crotch part and the waist opening provided by edges, with respect to a front-back direction of the diaper, of the front part and the back part.

Concerning names of respective parts of the diaper main body, a part applied to an abdomen side of a wearer is called the front part, a part applied to a buttocks side of the wearer is called the back part, and a part positioned between the front part and the back part and applied to a crotch of the wearer is called the crotch part, in a state of wearing the pants-type disposable diaper. The crotch part is a middle part when the pants-type disposable diaper is divided into three parts in the front-back direction in a state where the front part and the back part of the diaper are disjoined and the diaper is developed on a plane, and the crotch part is a part whose side edges in the width direction are not joined when the diaper is formed in a shape of pants. Thus, the leg openings are formed on only both sides of the crotch part.

The front-back direction means a direction from the front part toward the back part and vice versa of the pants-type disposable diaper. The term "front" means a direction from the back part toward the front part, and the term "back" means a direction from the front part toward the back part. The width direction means a direction orthogonal to the front-back direction on the same plane as the pants-type disposable diaper in a state where the pants-type disposable diaper is developed on a plane.

The pants-type disposable diaper of the present invention has an absorbent core disposed at the crotch part. The absorbent core is disposed at least at the crotch part, and further, may also extend to the front part and/or the back part.

In one embodiment of the diaper main body provided with the absorbent core, for example, a laminate comprising a liquid-permeable top sheet, a liquid-impermeable back sheet, and the absorbent core interposed therebetween may have the front part, the back part and the crotch part therebetween. In another embodiment of the diaper main body provided with the absorbent core, the diaper main body having the front part, the back part and the crotch part therebetween may be formed from a laminate comprising an inner sheet and an outer sheet; and an absorbent body in which the absorbent core is interposed between a liquid-permeable top sheet and a liquid-impermeable back sheet may be provided on an inner surface, that faces a wearer in wearing, of the inner sheet.

The top sheet is preferably made of a liquid-permeable material, and the back sheet is preferably made of a liquid-impermeable or water-repellent material. The inner sheet is preferably made of a hydrophilic or water-repellent material, and the outer sheet is preferably made of a water-repellent material.

The absorbent core is not particularly limited as long as it absorbs liquid excrement such as urine and the like, and it preferably contains an absorbent resin. The absorbent core can be obtained, for example, by the steps of mixing a granular absorbent resin with a hydrophilic fiber assembly such as crushed pulp fibers, cellulose fibers and the like to obtain a clump, or dispersing the granular absorbent resin to the hydrophilic fiber assembly to obtain a clump; wrapping the clump with a paper sheet such as a tissue paper and the like, or with a cover sheet such as a liquid-permeable nonwoven fabric sheet and the like; and molding the obtained wrapped clump into a predefined shape such as a rectangular shape, an hourglass shape, a center nipped-in gourd shape, a battledore shape, and the like.

The pants-type disposable diaper of the present invention comprises a first elastic member disposed so as to extend across the crotch part and along edges of a front side of the both leg openings, and a second elastic member disposed so as to extend across the crotch part and along edges of a back side of the both leg openings. Thus, the first elastic member has a first crotch-crossing part which extends across the crotch part and a first leg opening edge part which extends along the edges of the front side of the both leg openings; and the second elastic member has a second crotch-crossing part which extends across the crotch part and a second leg opening edge part which extends along the edges of the back side of the both leg openings. Each of the first and second leg opening edge parts has two portions, that is, one portion disposed along the edges of the right leg openings of the pants-type disposable diaper and the other portion disposed along the edges of the left leg openings of the pants-type disposable diaper. Both ends of the crotch-crossing part connect the each leg opening edge part.

The first and second elastic members are disposed at least at the crotch part, and further, may also extend to the front part and/or the back part. Preferably, the first and second elastic members extend to a part where the front part and the back part are joined.

The second elastic member is provided so as to be spaced from the first elastic member wholly. Thus, the first elastic member and the second elastic member neither contact nor intersect each other.

The first and second leg opening edge parts are respectively disposed continuously. The first leg opening edge part and the second leg opening edge part cooperate with each other to form leg gathers around a leg of a wearer, resulting in preventing leakage of excrement such as urine, loose stool and the like from the crotch part. The first and second leg opening edge parts mean parts where the first and second elastic member are disposed along the edges of the leg openings. The first and second leg opening edge parts are not necessarily disposed at the absolute edges of the leg openings, but are generally located at 5 mm or more inward from the edges of the leg openings.

Concerning the crotch-crossing part, the first crotch-crossing part is disposed intermittently, whereas the second crotch-crossing part is disposed continuously. Thus, the second elastic member is disposed continuously so as to extend across the crotch part and along edges of the back side of the both leg openings.

Due to the second elastic member which is disposed continuously so as to extend across the crotch part and along edges of the back side of the both leg openings, a pocket which extends from the second crotch-crossing part to the second leg opening edge part is formed at the bottom of the diaper or on the back side of the diaper. In the pants-type disposable diaper of the present invention, since the second elastic member is disposed so as to be spaced from the first elastic member, and the first elastic member is disposed so as to extend intermittently across the crotch part, stretching and contracting of the second elastic member are less likely to be impaired by the first elastic member, and hence, the suitable pocket is easily formed by the second elastic member. Concerning the pocket, if the first elastic member is also disposed continuously throughout, for example, the second crotch-crossing part of the second elastic member is pulled toward the first elastic member, and the deep pocket is unlikely to be formed. However, in the pants-type disposable diaper of the present invention, since the first crotch-crossing part of the first elastic member is disposed intermittently across the crotch part, the deeper pocket is easily formed by the second elastic member.

The pocket formed by the second elastic member serves to receive loose stool or diarrhea stool which contain a large amount of water. Loose stool or diarrhea stool contain a large amount of water and have high fluidity, but are absorbed by the absorbent core more slowly than urine. Therefore, in a general disposable diaper, loose stool or diarrhea stool may spread in a wide range on the diaper, thereby making the buttocks of a wearer dirty in a wide range, and may laterally leak from the diaper. However, in the pants-type disposable diaper of the present invention, loose stool or diarrhea stool can be received in the pocket formed by the second elastic member, and then the absorbent core is permitted to slowly absorb water contained in the loose stool or the diarrhea stool. Thus, loose stool or diarrhea stool are less likely to spread in a wide range on the diaper, and discomfort given to a wearer or a caregiver can be alleviated. In addition, lateral leakage of loose stool or diarrhea stool from the diaper is less likely to occur.

Further, in the pants-type disposable diaper of the present invention, since the first elastic member is disposed so as to extend intermittently across the crotch part, the contraction force of the first crotch-crossing part of the first elastic member is reduced, whereby the appearance of the front side of the diaper becomes simple and improved.

In order that loose stool or diarrhea stool may be received appropriately in the pocket formed by the second elastic member, a frontmost part of the second crotch-crossing part is preferably located at a region of 90 mm or less anterior and 40 mm or less posterior (more preferably at a region of 0 mm or more and 50 mm or less anterior) to a center of the diaper main body in the front-back direction. Here, the crotch-crossing part means a part extending across the crotch part and located at 30 mm or more inward from the edges of the leg openings. The center of the diaper main body in the front-back direction means a center line between the edges of the waist opening on the front and back parts in a state where the front part and the back part of the pants-type disposable diaper are disjoined from each other and the diaper main body is developed on a plane, and is normally located at the bottom of the diaper. The center of the diaper main body in the front-back direction is determined in a state where the diaper is fully spread, namely, in a state where the elastic member of the diaper is fully stretched.

The second elastic member is preferably spaced from the first elastic member at a distance of 10 mm or more and 50 mm or less (more preferably at a distance of 20 mm or more and 40 mm or less). When the second elastic member is spaced from the first elastic member at the distance of 50 mm or less, the leg gathers are formed appropriately along the edges of the both leg openings, resulting in preventing leakage of excrement such as urine, loose stool and the like from the crotch part certainly. When the second elastic member is spaced from the first elastic member at the distance of 10 mm or more, stretching and contracting of the second elastic member are less likely to be impaired by the first elastic member, thereby forming the pocket by the second elastic member appropriately. In addition, it becomes easy to provide the second crotch-crossing part continuously while providing the first crotch-crossing part intermittently.

The distance by which the second elastic member is spaced from the first elastic member means a minimum value of a distance between the first elastic member and the second elastic member in the front-back direction of the diaper. Preferably, the distance coincide with a distance between a backmost part of the first elastic member and a frontmost part of the second elastic member.

The second crotch-crossing part preferably includes the frontmost part of the second elastic member. In this case, the second elastic member is provided in a shape that is convex toward the front side of the diaper. As a result, loose stool or diarrhea stool are easily received appropriately in the pocket formed by the second elastic member. The first crotch-crossing part preferably includes the backmost part of the first elastic member.

The first and second elastic members may consist of one or a plurality of elastic members; and preferably consist of 2 to 5 of elastic members, respectively. In the case that the first and second elastic members consist of a plurality of elastic members, even if one elastic member is broken, the remaining elastic member(s) can maintain stretch and elastic properties. In addition, by disposing a plurality of elastic members side by side, wearing feel can be made soft while maintaining a high stretching force.

The first and second elastic members are preferably disposed to the diaper main body in a stretched state. Specifically, the second elastic member is preferably disposed to the diaper main body in a stretched state from one portion of the second leg opening edge part through the second crotch-crossing part to the other portion of the second leg opening edge part, and fixed to the diaper main body by means of an adhesive or the like. The first elastic member is preferably disposed to the diaper main body in a stretched state from one portion of the first leg opening edge part through the first crotch-crossing part to the other portion of the first leg opening edge part, and the first crotch-crossing part is preferably cut after at least the first leg opening edge part is fixed to the diaper main body by means of an adhesive or the like. Here, in light of manufacturing efficiency, it is preferred that the first crotch-crossing part is also fixed to the diaper main body by means of an adhesive or the like and then cut at multiple locations. The cutting of the first crotch-crossing part may be performed, for example, by holding the diaper main body, in which the elastic member is disposed, between a flat roll and a roll cutter having multiple cutting blades on its surface, and then forwarding it.

The first and second elastic members are preferably provided between two sheets. For example, when the diaper main body is composed of a laminate comprising a liquid-permeable top sheet, a liquid-impermeable back sheet, and an absorbent core interposed therebetween, respective elastic members are preferably disposed between the top sheet and the back sheet. When the diaper main body is composed of a laminate comprising an inner sheet and an outer sheet; and an absorbent body in which an absorbent core is interposed between a top sheet and a back sheet is provided on the surface of the inner sheet on a wearer side, the respective elastic members are preferably provided between the inner sheet and the outer sheet.

The pants-type disposable diaper of the present invention preferably comprises rising flaps provided along edges of opposite sides, with respect to the width direction, of the absorbent core. The rising flaps enable to prevent lateral leakage of urine, loose stool and the like certainly.

The rising flaps, for example, may be provided on an upper surface of the absorbent core at both sides in the width direction, or may be provided outside the absorbent core in the width direction. In the embodiment that the absorbent core is interposed between the top sheet and the back sheet, the rising flaps are joined, for example, to the top sheet, the back sheet folded back to an upper surface of the top sheet, or both the top sheet and the back sheet. The rising flaps are preferably made of a liquid-impermeable plastic film, a water-repellent nonwoven fabric, or the like, and more preferably made of a water-repellent nonwoven fabric.

A rising elastic member is preferably disposed at an upper end (an end nearer to a wearer) of the rising flap in a state of rising. The rising flap forms a rising gather which rises toward a wearer due to a contraction force of the rising elastic member, thereby preventing lateral leakage of urine, loose stool and the like. An inner surface of the rising flap may be joined to the top sheet at ends, with respect to the front-back direction of the diaper, of the rising flaps, thereby preventing leakage of urine, loose stool and the like in the front-back direction.

The pants-type disposable diaper of the present invention may further comprise a waist elastic member disposed along the edge of the waist opening, and a body elastic member disposed in the front part and the back part so as to extend in the width direction of the diaper, in addition to the first and second elastic members. The waist elastic member prevents excrement such as urine and the like from leaking from a back side or an abdomen side, even when a wearer lies. The body elastic member improves a fitting property of the diaper around an abdomen region. The waist elastic member and the body elastic member are preferably provided between two sheets, similarly to the first and second elastic members.

Elastic materials such as a polyurethane thread, a polyurethane film, a natural rubber and the like, which are generally used for disposable diapers, can be used for the respective elastic members. The respective elastic members are preferably fixed in a stretched state with a hot-melt adhesive. For example, a polyurethane thread having a fineness of 100 dtex to 2,500 dtex is stretched at a ratio of 1.1 to 5.0 times to be fixed. A preferable hot-melt adhesive is a rubber hot-melt adhesive.

Next, an example of the pants-type disposable diaper of the present invention is explained, referring to drawings. However, the present invention is not restricted to the following embodiment.

Figure 2:
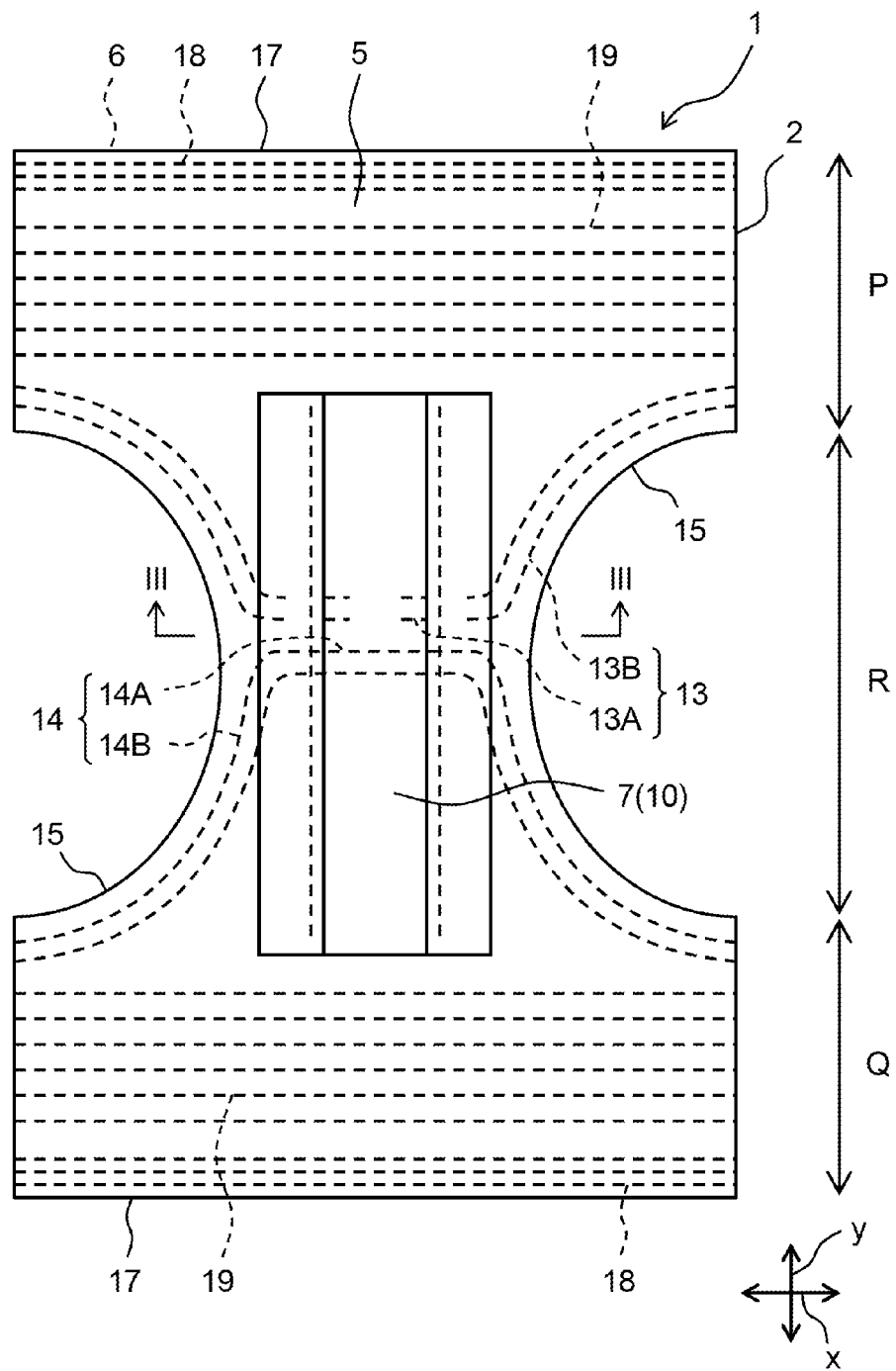
FIG. 2 shows a plan view of the pants-type disposable diaper shown in FIG. 1 in a developed state in which a front part and a back part are disjoined.
Figure 3:
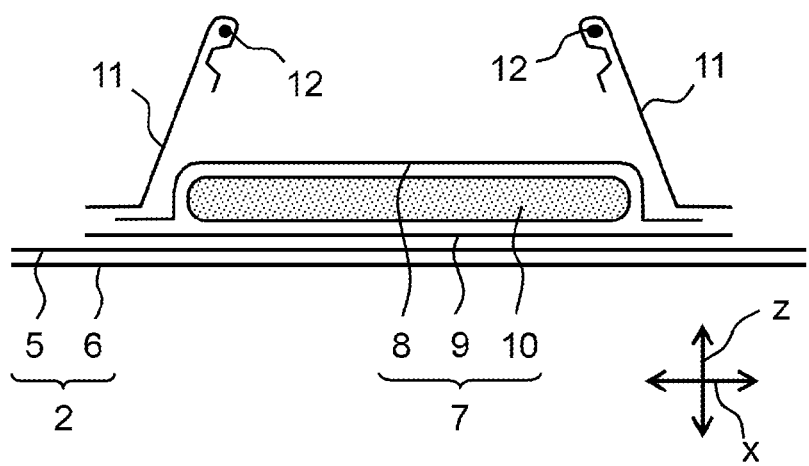
FIG. 3 shows a cross-sectional view taken along line in FIG. 2.
Figure 4:
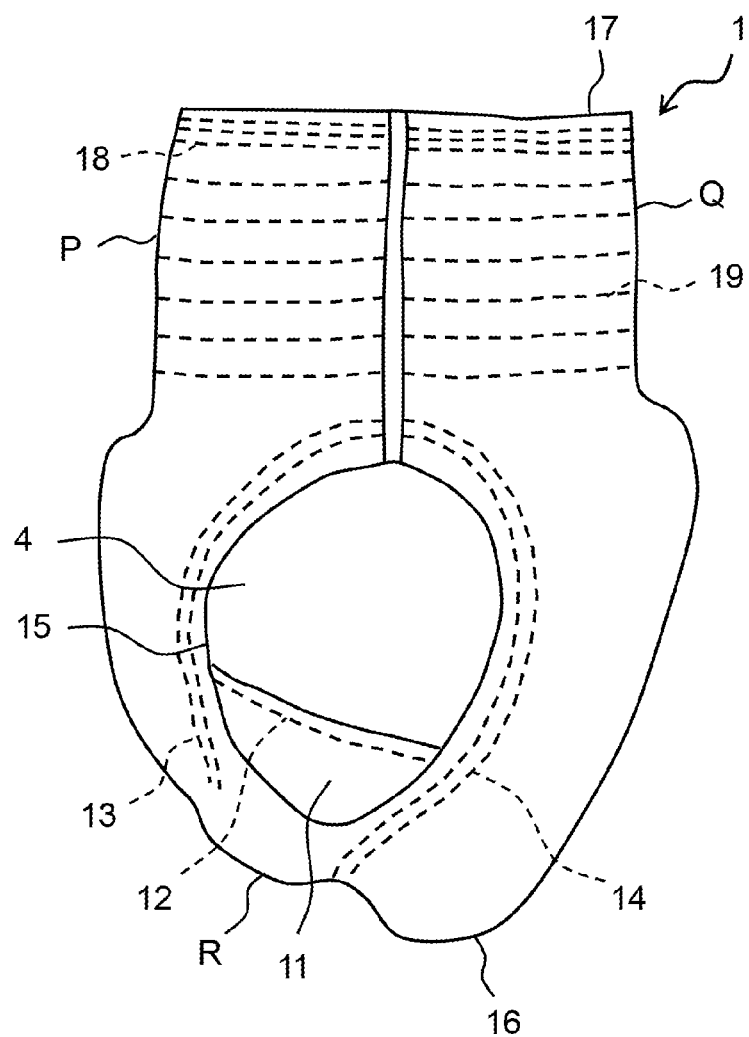
FIG. 4 shows a lateral view of the pants-type disposable diaper shown in FIG. 1.

FIG. 1 shows a perspective view of a pants-type disposable diaper of the present invention. FIG. 2 shows a plan view of the pants-type disposable diaper shown in FIG. 1 in a developed state in which a front part and a back part are disjoined. FIG. 3 shows a cross-sectional view taken along line III-III in FIG. 2. FIG. 4 shows a lateral view of the pants-type disposable diaper shown in FIG. 1. In the drawings, the arrow x direction represents a width direction of the diaper, and the arrow y represents a front-back direction of the diaper. The direction perpendicular to the plane formed by the arrows x and y is defined as a thickness direction z.

A pants-type disposable diaper 1 comprises a diaper main body 2 having a front part P, a back part Q, and a crotch part R positioned between the front part P and the back part Q, and having a waist opening 3 and a pair of leg openings 4 formed by joining the front part P and the back part Q. The diaper main body 2 is composed of a laminate comprising an inner sheet 5 and an outer sheet 6.

The pants-type disposable diaper 1 comprises an absorbent core 10 disposed at the crotch part R. In detail, the pants-type disposable diaper 1 comprises an absorbent body 7 disposed on an inner surface of the diaper main body 2 at the crotch part R and comprising a top sheet 8, a back sheet 9, and an absorbent core 10 interposed between the top sheet 9 and the back sheet 10, as shown in FIG. 3. The top sheet 8 is placed so as to face a wearer's skin at a crotch, and allows excrement such as urine, loose stool and the like to permeate through. The excrement that permeated the top sheet 8 is accommodated in the absorbent core 10. The back sheet 9 is attached to the inner sheet 5 of the diaper main body 2, and prevents the excrement from permeating outside.

Rising flaps 11 are provided along edges of opposite sides, with respect to the width direction x, of the absorbent core 10 (FIG. 3). The rising flap 11, which extends in the front-back direction y of the diaper, is joined astride the top sheet 8 and the back sheet 9. A rising elastic member 12 is disposed at an inner end in the width direction x of the rising flap 11. A rising gather which rises upward (toward a wearer) is formed from the rising flap 11 due to a contraction force of the rising elastic member 12, thereby preventing lateral leakage of urine, loose stool and the like. An inner surface of the rising flaps 11 is joined to the top sheet 8 at front and back ends of the absorbent body 7, thereby preventing leakage of urine, loose stool and the like outward in the front-back direction y.

A first elastic member 13 is disposed to the diaper main body 2 so as to extend across the crotch part R and along edges 15 of a front side of the both leg openings 4. The first elastic member 13 has a first crotch-crossing part 13A which extends across the crotch part R and a first leg opening edge part 13B which extends along the edges 15 of the front side of the both leg openings 4. In the first elastic member 13, the first crotch-crossing part 13A is disposed intermittently, whereas the first leg opening edge part 13B is disposed continuously. The first elastic member 13 is provided between the inner sheet 5 and the outer sheet 6. Because the first elastic member 13 is not recognized directly in appearance, even a part which is disposed continuously is shown as a dashed line.

A second elastic member 14 is disposed to the diaper main body 2 so as to be spaced from the first elastic member 13 and extend across the crotch part R and along edges 15 of a back side of the both leg openings 4. The second elastic member 14 has a second crotch-crossing part 14A which extends across the crotch part R and a second leg opening edge part 14B which extends along the edges 15 of the back side of the both leg openings 4. In the second elastic member 14, both of the second crotch-crossing part 14A and the second leg opening edge part 14B are disposed continuously. The second elastic member 14 is provided between the inner sheet 5 and the outer sheet 6. Here, though the second elastic member 14 is disposed continuously, it is shown as a dashed line in the drawing because it is not recognized directly in appearance. A frontmost part of the second crotch-crossing part 14A of the second elastic member 14 is located at a region of 90 mm or less anterior and 40 mm or less posterior to a center of the diaper main body 2 in the front-back direction y.

In the pants-type disposable diaper 1, a pocket 16 is formed on the back side of the pants-type disposable diaper 1 by the second elastic member 14, as shown in FIG. 4. Loose stool or diarrhea stool can be received appropriately in the pocket 16. The first leg opening edge part 13B of the first elastic member 13 and the second leg opening edge part 14B of the second elastic member 14 cooperate with each other to form leg gathers along the edges 15 of the both leg openings 4, thereby preventing leakage of excrement such as urine, loose stool and the like from the crotch part R.

In the diaper main body 2, a waist elastic member 18 is disposed along an edge 17 of the waist opening 3, and a body elastic member 19 is disposed in the front part P and the back part Q so as to extend in the width direction x of the diaper. The waist elastic member 18 and the body elastic member 19 are also provided between the inner sheet 5 and the outer sheet 6.

REFERENCE SIGNS LIST

1: a pants-type disposable diaper
2: a diaper main body
10: an absorbent core
13: a first elastic member
14: a second elastic member
16: a pocket

The invention claimed is:
1. A pants-type disposable diaper comprising:
a diaper main body having a front part, a back part, and a crotch part positioned between the front part and the back part, and having a waist opening and a pair of leg openings formed by joining the front part and the back part;
an absorbent core disposed at the crotch part;
a first elastic member disposed to the diaper main body, and having a first crotch-crossing part which extends intermittently across the crotch part and a first leg opening edge part which extends along edges of a front side of the both leg openings; and
a second elastic member disposed continuously to the diaper main body so as to be spaced from the first elastic member, and having a second crotch-crossing part which extends across the crotch part and a second leg opening edge part which extends along edges of a back side of the both leg openings.

2. The pants-type disposable diaper according to claim 1, wherein frontmost part of the second crotch-crossing part is located at a region of 90 mm or less anterior and 40 mm or less posterior to a center of the diaper main body in a front-back direction.

3. The pants-type disposable diaper according to claim 1, wherein the second elastic member is spaced from the first elastic member at a distance of 10 mm or more and 50 mm or less.

4. The pants-type disposable diaper according to claim 2, wherein the second elastic member is spaced from the first elastic member at a distance of 10 mm or more and 50 mm or less.

5. The pants-type disposable diaper according to claim 1, wherein both ends of the first crotch-crossing part connect to the first leg opening edge part.

6. The pants-type disposable diaper according to claim 1, wherein the first leg opening edge part and the second leg opening edge part cooperate with each other to form leg gathers around the leg openings.

* * * * *